United States Patent
Dufresne (10) Patent No.: US 9,885,696 B2
(45) Date of Patent: Feb. 6, 2018

(54) SYSTEM FOR ANALYZING MERCURY

(71) Applicant: Philip J. Dufresne, Lakewood, OH (US)

(72) Inventor: Philip J. Dufresne, Lakewood, OH (US)

(*) Notice: Subject to any disclaimer, the term of this patent is extended or adjusted under 35 U.S.C. 154(b) by 35 days.

(21) Appl. No.: 14/896,964

(22) PCT Filed: Jun. 19, 2014

(86) PCT No.: PCT/US2014/043191
§ 371 (c)(1),
(2) Date: Dec. 9, 2015

(87) PCT Pub. No.: WO2014/205222
PCT Pub. Date: Dec. 24, 2014

(65) Prior Publication Data
US 2016/0123946 A1 May 5, 2016

Related U.S. Application Data (60) Provisional application No. 61/837,694, filed on Jun. 21, 2013.

(51) Int. Cl.
*G01N 21/00* (2006.01)
*G01N 33/00* (2006.01)
(Continued)

(52) U.S. Cl.
CPC ......... *G01N 33/0045* (2013.01); *G01N 21/01* (2013.01); *G01N 21/3103* (2013.01); *G01N 2021/3107* (2013.01)

(58) Field of Classification Search
CPC ........... G01N 2021/3107; G01N 21/01; G01N 21/3103; G01N 33/0045
(Continued)

(56) References Cited

U.S. PATENT DOCUMENTS 3,281,596 A * 10/1966 Williston ........... G01N 21/3103
250/304
5,045,476 A 9/1991 Huber
(Continued)

FOREIGN PATENT DOCUMENTS

DE 195 06 875 C1 10/1996
EP 2 369 335 A1 9/2011
JP 2010-096688 A 4/2010

OTHER PUBLICATIONS

EP 14 813 771.4 Supplementary Search Report, dated Feb. 10, 2017.
(Continued)

*Primary Examiner* — Tri T Ton
(74) *Attorney, Agent, or Firm* — Fay Sharpe LLP (57) ABSTRACT

An analyzer system (10) for measuring the mercury content of samples includes a mercury vapor analyzer (12) for generating and detecting analytical beams. A furnace (24) is mounted to a measurement cell (22). A sample boat (30) containing a sample is adapted to be disposed within the furnace to release heated sample effluent gas from the sample into the measurement cell. An optical bench (16) mounted to the mercury vapor analyzer (12) into which the measurement cell (22) is positioned in a path traveled by the analytical beams projected out of the vapor analyzer whereby the analytical beams traverse the measurement cell, interact with the sample effluent gas and return back to the vapor analyzer (12) where the amount of mercury in the heated sample effluent gas can be determined. A pump station (56) to draw the sample effluent gas from the measurement cell.

22 Claims, 9 Drawing Sheets

(51) Int. Cl.
  *G01N 21/01* (2006.01)
  *G01N 21/31* (2006.01)
(58) Field of Classification Search
  USPC .................................................. 356/432–448
  See application file for complete search history.

(56) References Cited

U.S. PATENT DOCUMENTS

| | | |
|---|---|---|
| 5,619,041 A | 4/1997 | Hoffmann et al. |
| 5,879,948 A | 3/1999 | Van Pelt et al. |
| 6,223,584 B1 | 5/2001 | Mustacich et al. |
| 2003/0110950 A1 | 6/2003 | Sjostrom et al. |
| 2006/0245973 A1 | 11/2006 | Kita et al. |
| 2011/0026020 A1 | 2/2011 | Sholupov |
| 2012/0011512 A1 | 1/2012 | Peckham et al. |
| 2012/0194818 A1 | 8/2012 | Disch |

OTHER PUBLICATIONS

Mercury Instruments USA "Mercury Laboratory Analyzer LA 254", May 30, 2013 (May 30, 2013), XP055340193, retrieved from the internet: URL:http//web.archive.org/web/20130530311058/http://www.mercury-instrumentsusa.com/254.html, retrieved on Jan. 30, 2017. (whole document).
PCT/US2014/043191 International Search Report, dated Nov. 3, 2014.

\* cited by examiner

SYSTEM FOR ANALYZING MERCURY

TECHNICAL FIELD OF THE INVENTION

The present invention relates to a system for measuring mercury in samples of various matrices such as gaseous, aqueous, complex such as oils, and solids including sorbent traps used to measure the mercury concentration from emission sources such as coal-fired power plants, cement kilns and other emission sources.

BACKGROUND OF THE INVENTION

Mercury vapor analyzers with attachments to be used to analyze mercury vapor as well as other matrices including solids (including sorbent traps), waters and oil, have a number of drawbacks specifically relating to the speed that samples can be prepared, analyzed and the accuracy of the readings. There is a need for an attachment that can be used with a mercury vapor analyzer, as well as many other types of analyzers such as but not limited to the atomic absorption analyzers, Zeeman atomic absorption analyzers, and atomic fluorescence analyzers to address these shortcomings.

SUMMARY OF THE INVENTION

According to the present invention, there is disclosed an analyzer system for measuring mercury including a mercury vapor analyzer for generating and detecting analytical beams; a furnace mounted to a measurement cell; a sample boat adapted to be disposed within the furnace to release heated sample effluent gas from the sample into the measurement cell; an optical bench mounted to the mercury vapor analyzer into which a measurement cell is in a path traveled by the analytical beams projected out of the vapor analyzer whereby the analytical beams traverse the measurement cell, interact with the heated sample effluent gas and return back to the vapor analyzer where the amount of mercury in the sample effluent gas can be determined; and a pump station to draw the sample effluent gas from the measurement cell.

Further according to the present invention, there is disclosed an analyzer system for measuring mercury within aqueous samples, including: a mercury vapor analyzer for generating and detecting analytical beams; an impinger for mixing aqueous samples containing mercury with a stannous chloride solution, the impinger including a vessel closed with a cap having an air inlet and an outlet; a measurement cell connected at a first end to the outlet of the impinger and at a second end to a vacuum pumping system; and an optical bench mounted to the mercury vapor analyzer into which a measurement cell is placed in a path traveled by the analytical beams projected out of the vapor analyzer whereby the analytical beams traverse the measurement cell, interact with the sample effluent of the impinger directed into the cell from the outlet of the impinger and out of the cell through the outlet of the cell.

Still further according to the present invention, there is disclosed a method for measuring mercury, comprising the steps of: generating and detecting analytical beams with a mercury vapor analyzer; releasing heated sample effluent gas from a sample heated in a sample boat disposed within a furnace into the measurement cell; projecting the analytical beams from the vapor analyzer through the measurement cell to interact with the sample effluent gas and returning the analytical beams back to the vapor analyzer where the amount of mercury in the sample effluent gas can be determined; and drawing the sample effluent gas from the measurement cell.

DETAILED DESCRIPTION OF THE PREFERRED EMBODIMENTS

In the description that follows, numerous details are set forth in order to provide a thorough understanding of the present invention. It will be appreciated by those skilled in the art that variations of these specific details are possible while still achieving the results of the present invention. Well-known processing steps are generally not described in detail in order to avoid unnecessarily obfuscating the description of the present invention.

In the description that follows, exemplary dimensions may be presented for an illustrative embodiment of the invention. The dimensions should not be interpreted as limiting. They are included to provide a sense of proportion. Generally speaking, it is the relationship between various elements, where they are located, their contrasting compositions, and sometimes their relative sizes that is of significance.

In the drawings accompanying the description that follows, often both reference numerals and legends (labels, text descriptions) will be used to identify elements. If legends are provided, they are intended merely as an aid to the reader, and should not in any way be interpreted as limiting.

The present invention relates to an analyzer system 10 and 180 for measuring mercury in samples of various matrices such as solids including sorbent traps that have been used to collect the mercury from emission sources such as coal-fired power plants and cement kilns, and aqueous samples.

Figure 1:
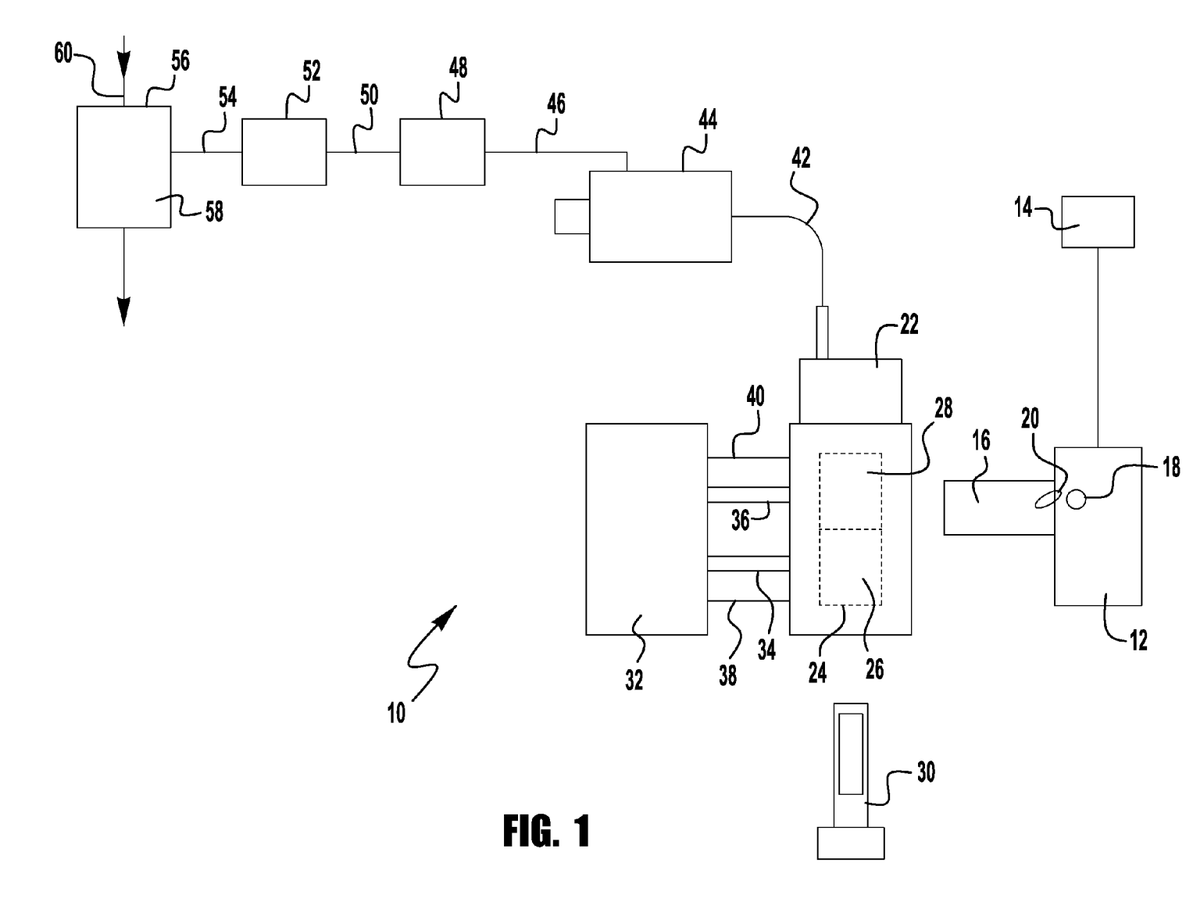
FIG. 1 is a schematic of an analyzer system, in accordance with the present invention.

As shown in FIG. 1, a schematic of analyzer system 10 for measuring mercury includes a commercial or custom mercury vapor analyzer 12 connected to a computer 14. An optical bench 16 (either single pass or multi-path) is securely mounted to the commercial or custom mercury vapor analyzer 12. The analyzer system 10 allows the mercury released from the samples with either thermal or aqueous apparatus (depending on the matrix of the sample) to be measured with the mercury vapor analyzer 12 and analyzed with the computer 14.

An optical bench 16 is securely fastened to the mercury vapor analyzer 12 so that the analytical beam(s) projected out of the analyzer can reliably travel from their source 18 and then back to the optical detector 20 in the mercury vapor analyzer 12. The optical bench 16 is disposed so that a measurement cell 22 can be placed in the path of the analytical beam(s) projected out from the mercury vapor analyzer 12. The analytical beams from source 18 can traverse the inside of the measurement cell 22 to interact with the sample effluent released in a furnace 24 and then return back to the optical detector 20 in the mercury vapor analyzer 12 to be analyzed with the computer 14.

The measurement cell 22 is mounted to a furnace 24 which can have two temperature sections 26 and 28 into which a sample boat 30 into which a sample such as, for example, a section of a sorbent trap can be disposed. The heat from the furnace 24 causes an effluent of sample gas from the sample to be released into measurement cell 22 for analysis by the mercury vapor analyzer 12.

A furnace controller 32 can be connected to furnace 24 by two power cords 34 and 36, to control the low and high temperature sections 26 and 28, respectively. Two thermocouples 38 and 40 are connected at one end to the low and high temperature sections 26 and 28, respectively, and at the other end to furnace controller 32 to control the temperature in each of the temperature sections.

A gas line 42 connects the measurement cell 22 to a thermo-electric cooled exhaust gas conditioner 44 which cools the heated sample gases generated in the furnace 24 and directed into the measurement cell 22. The heated sample gases are withdrawn from the measurement cell 22 through the gas line 42 and directed to the exhaust gas conditioner 44. The hot sample gases are cooled in the exhaust gas conditioner 44 so as to condense any excess moisture carried in the sample gases. This is important because the change in state from the steam in the heated sample gases to water can cause a change in the flow rate of the sample gases being withdrawn from the measurement cell 22. It is important that the water in the hot sample gases condense quickly before mercury comes out of the sample being tested.

The resulting exhaust gas at near ambient temperature then flows from the thermo-electric cooled, exhaust gas conditioner 44 through a gas line 46 to a filter 48 which contains soda lime, iodinated charcoal and or charcoal to scrub the sample gases of acid gases and mercury.

The resulting exhaust gas then flows from filter 48 through a gas line 50 and then through a mass flow controller 52, such as a Whisper series laminar flow element mass flow controller manufactured by Alicat Scientific, Inc. of Tucson, Ariz. The laminar flow element mass flow controller 52 precisely regulates the flow of gas through the analyzer system 10 despite the low differential pressure between the flow controller inlet and outlet inherent in this design. The mass flow controller 52 regulates by either mass or volume.

The sample gas is then drawn through a line 54 from the mass flow controller 52 into a pump station 56. The resulting sample gas exits the pump (not shown) located inside the pump station 56 through a line and passes through a muffler (not shown) which suppresses the sound of the exhaust. The pump station 56 includes a high powered pump which can pump >20 liters/minute (l/m) while the present embodiment may often, or at times only require a flow rate of a fraction of this flow amount. Therefore, the pump station 56 includes an air inlet 60 that can be controlled to allow more or less air through the pump station 56 into the pump to mix with the gases from line 54.

Figure 2:
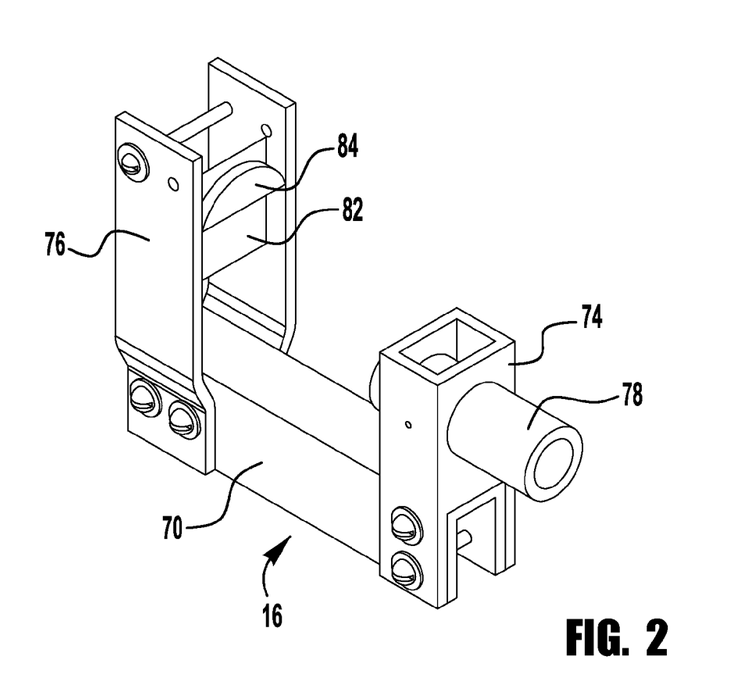
FIG. 2 is a three dimensional view of an optical bench, in accordance with the present invention.
Figure 4:
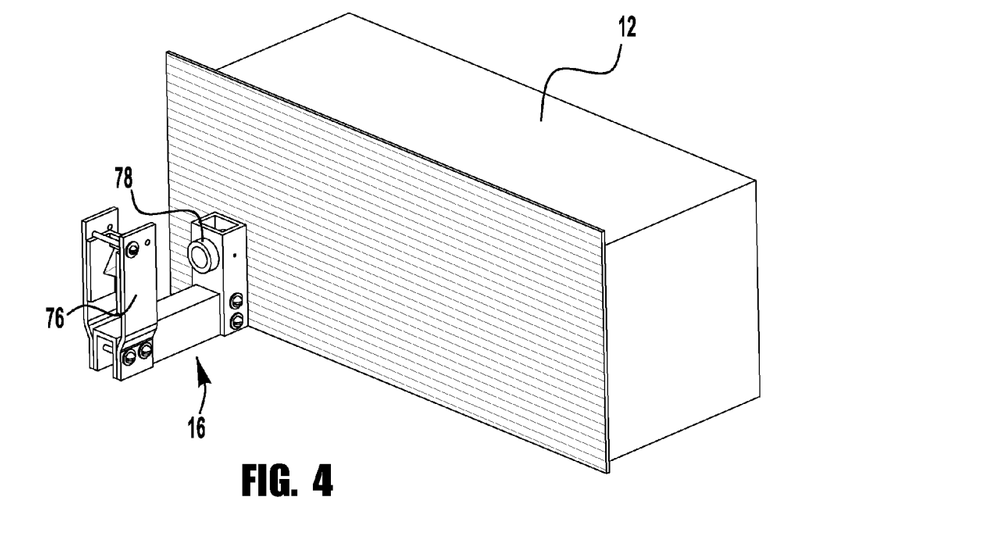
FIG. 4 is a three dimensional view of an optical bench mounted to an analyzer, in accordance with the present invention.

Referring to FIG. 2, there is illustrated a three dimensional view of the optical bench 16. A base support 70 can be a rectangular shaped tube having an upstanding tube support 74 mounted to one end and a prism/lens support 76 mounted to the opposite end. The upstanding tube support 74 includes a hollow tube 78 that is securely mounted into an opening formed in the side of the analyzer 12, as shown in FIG. 4. The outgoing beams generated by the beam source (not shown) in the analyzer 12 (compare 18 in FIG. 1) project through the hollow tube 78, pass through the measurement cell 22, as discussed hereinafter, and are turned 180 degrees on a separate path by the prism 82 mounted in the prism/lens support 76 and focused by the lens 84 so that they can travel back to an optical detector (not shown) located within the analyzer 12 and aligned with the tube 78.

Figure 3:
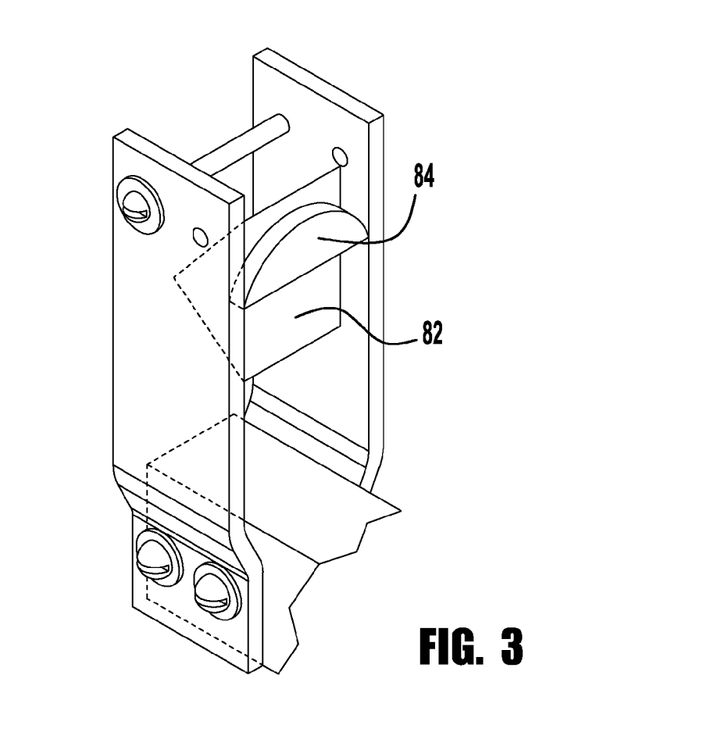
FIG. 3 is a side view of a lens and prism mounted at an end of the optical bench, in accordance with the present invention.

For the dual-path optical bench 16 where the beam's source 18 and optical detector 20 are located adjacent to each other, the lens 84 and prism 82, as shown in FIGS. 2 and 3, made of quartz (or other material transparent to the wavelengths of the beams used) are placed adjacent to each other such that the outgoing beams from the analyzer 12 pass through the cell 22, as discussed hereinafter, are turned 180 degrees on a separate path by the prism 82 and focused by the lens 84 so that the beams can travel back to the optical detector in the analyzer.

The length of the optical bench 16 is about 10 cm to about 20 cm and preferably about 15 cm to about 18 cm to work with the beam dispersion properties of the analyzer 12, such as a Lumex analyzer from Lumex Ltd. of St. Petersburg, Russia. But it is within the terms of the preferred embodiment that the optical bench 16 could be extended to about 35 cm with additional optical elements allowing the use of a measurement cell 180, see FIG. 13, of about 30 cm in length that would be beneficial for analyzing low-level water samples which would enable measurements of mercury in water at 0.5 nanogram (ng)/liter (L) or lower.

Figure 5:
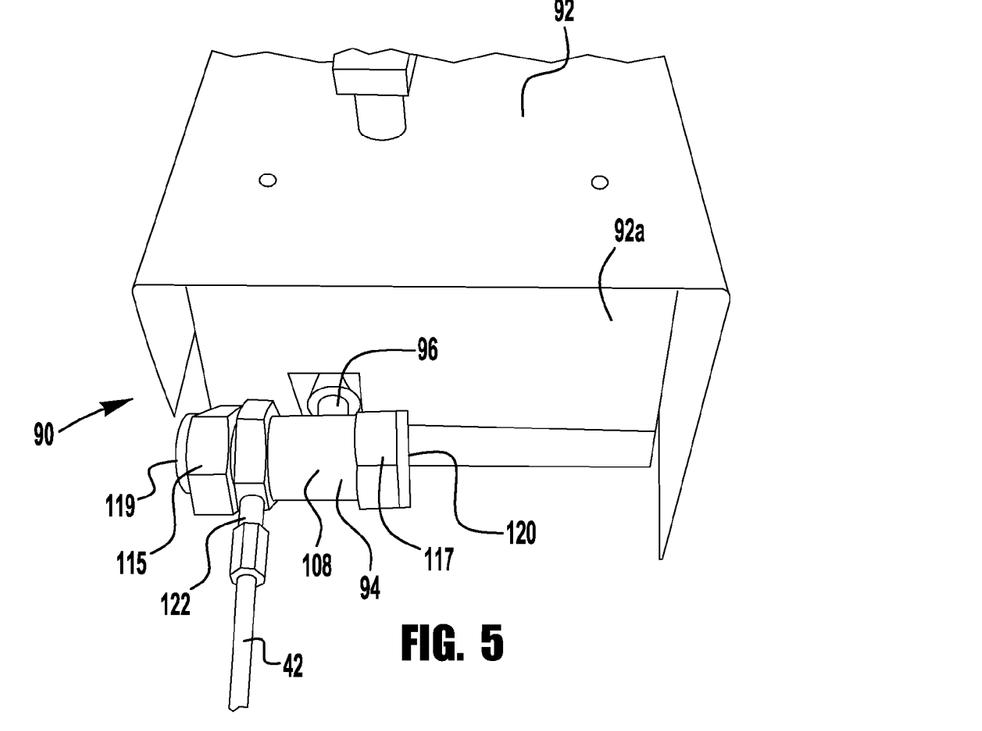
FIG. 5 is a three dimensional view of a thermal analysis device, in accordance with the present invention.

A key component of the present invention is the thermal analysis device 90, as shown in FIG. 5. The thermal analysis device 90 has an enclosed housing 92. A measurement cell 94 (compare 22 in FIG. 1) is mounted to a tubular fitting 96 which extends through a rear wall 92a of housing 92 and is mounted to an end of an oven component 100 (compare 24 in FIG. 1) disposed within the enclosed housing.

Figure 6:
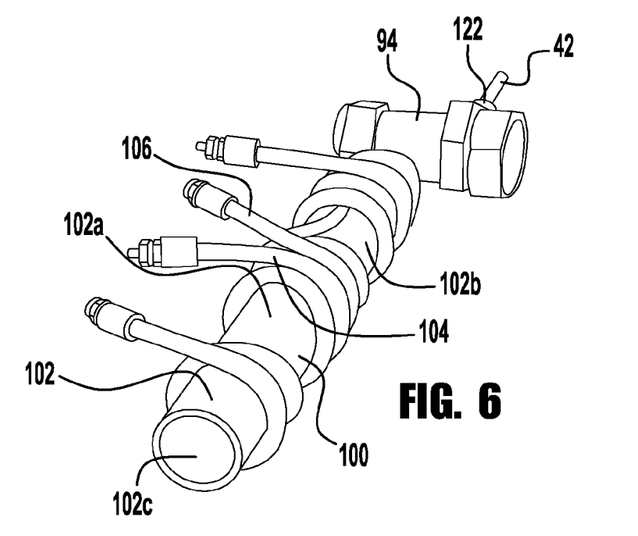
FIG. 6 is a three dimensional view of a measurement cell and furnace component, in accordance with the present invention.

As shown in FIG. 6, the oven or furnace component 100 is constructed of an elongated sample desorption tube 102 connected at one end to the tubular fitting 96 which in turn is mounted to the measurement cell 94. A first bendable resistance-heating coil 104 is tightly wrapped around a first heating section or heated zone 102a (compare 26 in FIG. 1) of the sample desorption tube 102 and a second bendable resistance-heating coil 106 is tightly wrapped around a second heating section or heated zone 102b (compare 28 in FIG. 1) of the sample desorption tube 102. The first resistance-heating coil 104 is disposed closer to the open end 102*c* of the tube 102 and the second resistance-heating coil 106 is disposed closer to the measurement cell 94. The open end 102*c* of the sample desorption tube 102 can be accessed through opening 95 through the wall of enclosed housing 92, as shown in FIG. 7.

Figure 7:
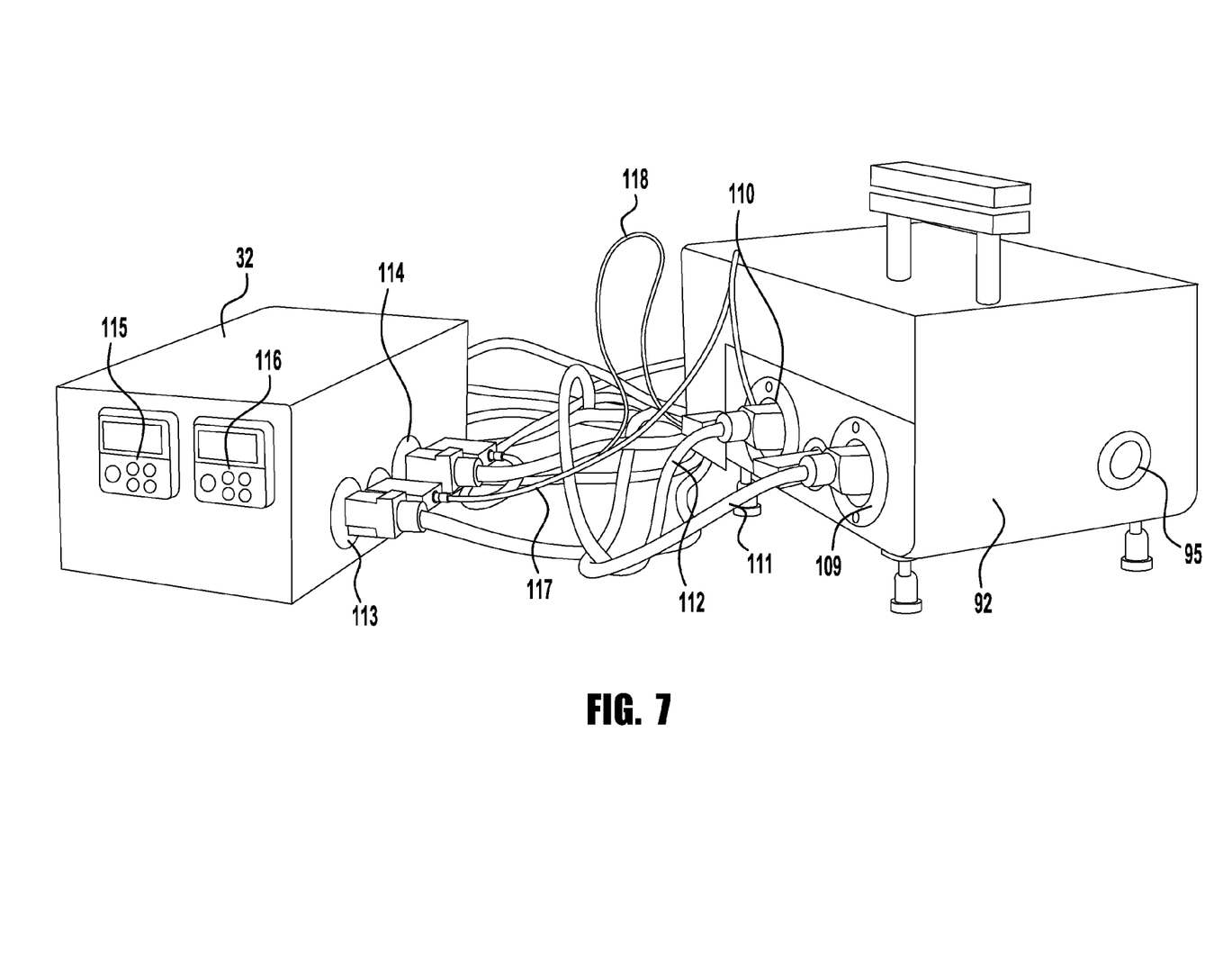
FIG. 7 is a three dimensional view of temperature controllers connected to the thermal analysis device, in accordance with the present invention.

The two heating coils 104 and 106 are connected via suitable high-temperature wires (not shown), to the receptacles 109, 110 that are in turn connected via power cords 111, 112, respectively, to wired receptacles 113, 114 which in turn are connected to relays controlled by the PID temperature controllers 115, 116 in the control device 32, as shown in FIG. 7. Two thermocouples (not shown) are secured inside the sample desorption tube 102, one placed to measure the temperature at the front or first heated zone 102*a* under the heating coil 104, the other at the rear or second heated zone 102*b* under the heating coil 106. The thermocouples are connected via receptacles and thermocouple wires 117, 118 to their respective PID controllers 115,116 in control device 32. The pair of heating coils 104, 106 allow the front zone 102*a* and the rear zone 102*b* of the sample desorption tube 102 to be at different temperatures or if needed, to ramp up the temperatures of one or the other or both of the front and/or rear heat zones, 102*a*,102*b*, respectively.

The measurement cell 94 (compare 22 in FIG. 1), as shown in FIG. 5, is constructed of a tube 108 mounted to the tubular fitting 96 and sealed on both ends by windows 119, 120 made of quartz or other suitable material transparent to the wavelengths used. Screw caps 115, 117 hold the windows 119,120 in place with washers and graphite gaskets pressing the windows onto additional gaskets made of graphite or other suitable material (not shown) so that the measurement cell 94 is essentially "air-tight" aside from the open end 102*c* at the end of the sample desorption tube 102, (see FIG. 6), and an exhaust outlet 122 in the back of the measurement cell 94 that is ideally offset from the tube 96 connecting the measurement cell to the sample desorption tube. The exposed screw-on window holders 115,117 make window removal and cleaning easier even when hot as compared to bayonet type fittings on other prior art instruments.

The thermal analysis device 90 consists of a hollow "T" shaped metal (stainless steel or other material inert to mercury at operating conditions) structure integrating the oven component 100 or sample desorption tube 102 with the measurement cell 94. The inner diameter of the sample desorption tube 102 is large enough so that air flowing though the tube from open end 102*c* at a high flow rate between about 4 L/minute and 40 L/minute does not sweep the sample out of a sample boat 30 disposed within the sample desorption tube 102.

Figure 11:
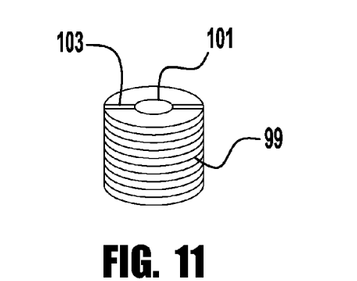
FIG. 11 is a three dimensional view of a flow modifier, in accordance with the present invention.

A flow modifier 99, as shown in FIG. 11, can be threaded into the tube 96 at the end of the sample desorption tube 102 using a slot 103. The flow modifier 99 has a passageway 101 extending there through so that the mercury containing gases passing through flow modifier 99 into the measurement cell 94 are induced into turbulent flow that better mixes the gas stream improving measurement precision. To further increase the turbulence, a length of wire (not shown) can be inserted into the passageway 101. Alternately, several through passageways (not shown) can be provided, with one or more of the passageways angled with respect to each other.

The oven component 100 heats the sample being tested in sample desorption tube 102 and the resulting effluents, as discussed in more detail hereinafter, to a temperature (usually between about 590 Celsius (C) to about 680 degrees C. In this temperature range, all the elemental mercury present in the sample is converted to the gaseous phase and all the mercury compounds of interest in the sample are broken down so the mercury is in the elemental form (also gaseous) and released into the air flow through sample desorption tube 102. The elemental mercury vapor is transported, through the analytical or measurement cell 94 disposed on the optical bench 16 connected to the analyzer 12, by means of a stream of air at a constant flow rate entering the open end 102*c* of oven component 100 and exiting the measurement cell 94 through an outlet port 122 into line 42. This stream of air is created by the pump station 56.

Figure 8A:
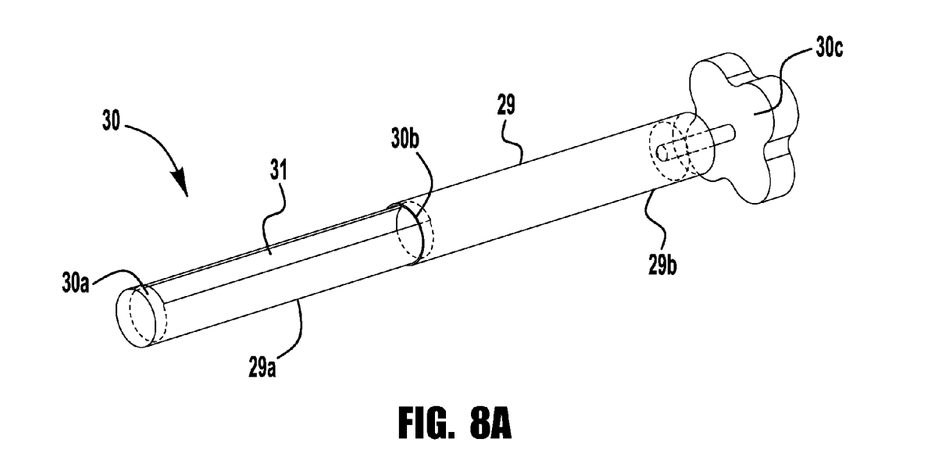
FIG. 8A is a three dimensional view of a sample containment boat, in accordance with the present invention.
Figure 8B:
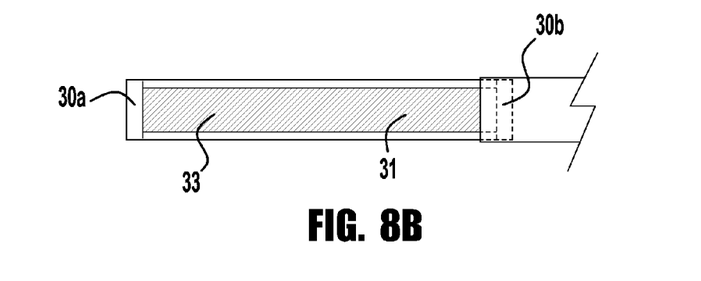
FIG. 8B is a three dimensional view showing the top view of the sample containment boat, in accordance with the present invention.

The sample being tested is placed in a sample containment boat 30, as shown in FIGS. 1, 8A and 8B. The sample containment boat 30 is placed into the oven component 100 through opening 95 in a wall of the enclosed housing 92 and then into the open end 102*c* of the sample desorption tube 102. The flow rate of air through the oven component 100 is constant. The unique plumbing of the preferred embodiment allows a single pump station 56 to provide flow rates ranging from between about 0.5 L/min to about 20 L/min, and it controls the flow rates well. The mercury vapor analyzer 12 can then measure the total mercury content of the sample by analyzing the beams passing through the measurement cell 94.

A typical sample boat 30, as shown in FIGS. 8A and 8B, is made of a stainless steel tube 29 and with an elongated opening 31 into the tube forming an open slot 33 at the sample end 29*a* of the boat. Stainless steel plugs 30*a* and 30*b* are provided at each end of the open slot 33. A heat resistant handle 30*c* is disposed at the opposite end 29*b* of the sample boat 30 so that the sample boat can be comfortably handled even when the sample end 29*a* of the boat has been heated to 700 degrees C. for a reasonable length of time. It is also within the terms of the preferred embodiment that traditional sample boats of quartz and ceramic can be used in the oven compartment or furnace 100.

The length of ideal boats 30 is such that they can be initially inserted into the furnace 100 with the sample end 29*a* in the first zone 102*a* beneath the heating coil 104 with stability and then further inserted so that the sample end 29*a* of the boat is disposed within the second zone 102*b* beneath the heating coil 106.

Since the resistance-heating coils 104 and 106 are electrically isolated from the sample desorption tube 102, sample boats 30 made of metal can be used without shorting out the heating coils. Metal boats are more durable than those of ceramic or quartz and will not vitrify and break as quartz boats will.

Referring again to FIG. 6, the oven component 100 of the thermal analysis accessory 90 is illustrated with a large sample tube 102. The larger design allows higher flows without disturbing the sample components placed in the sample containment boat 30; it also accommodates larger boats that can carry larger samples, and it makes all samples easier to analyze.

Figure 9:
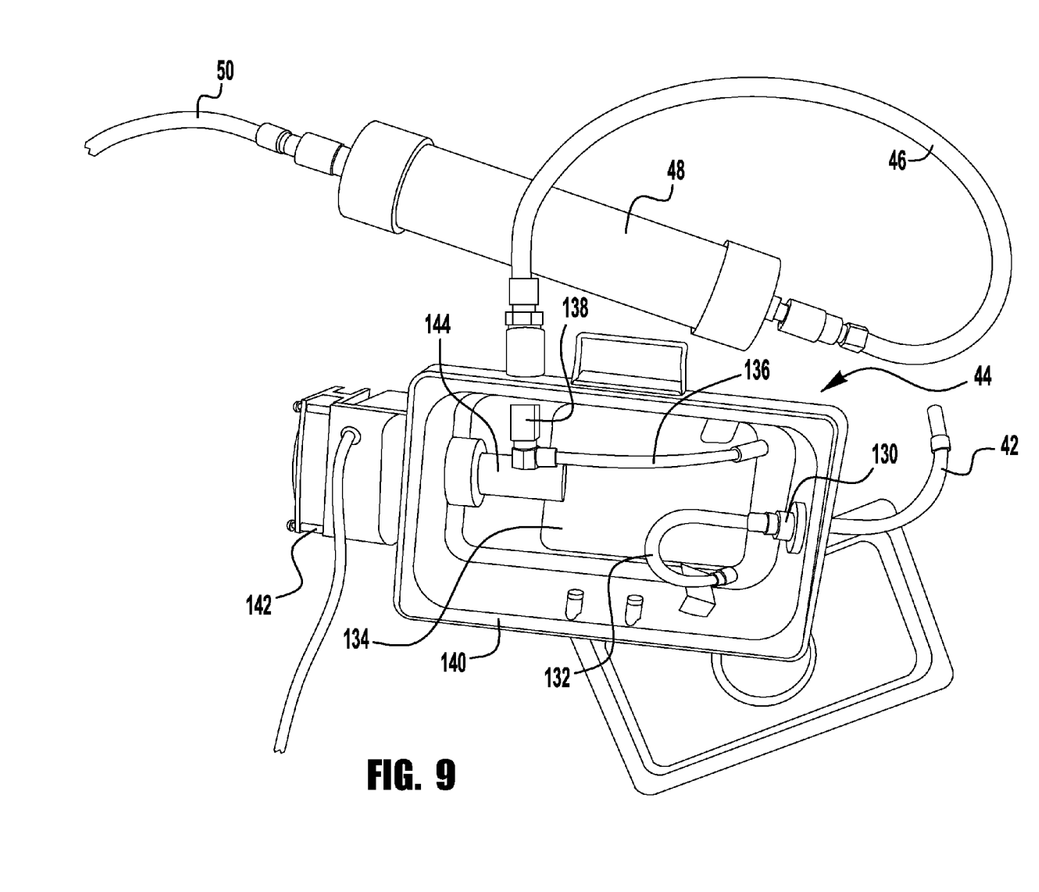
FIG. 9 is a three dimensional view of an exhaust gas conditioner connected to a filter, in accordance with the present invention.
Figure 10:
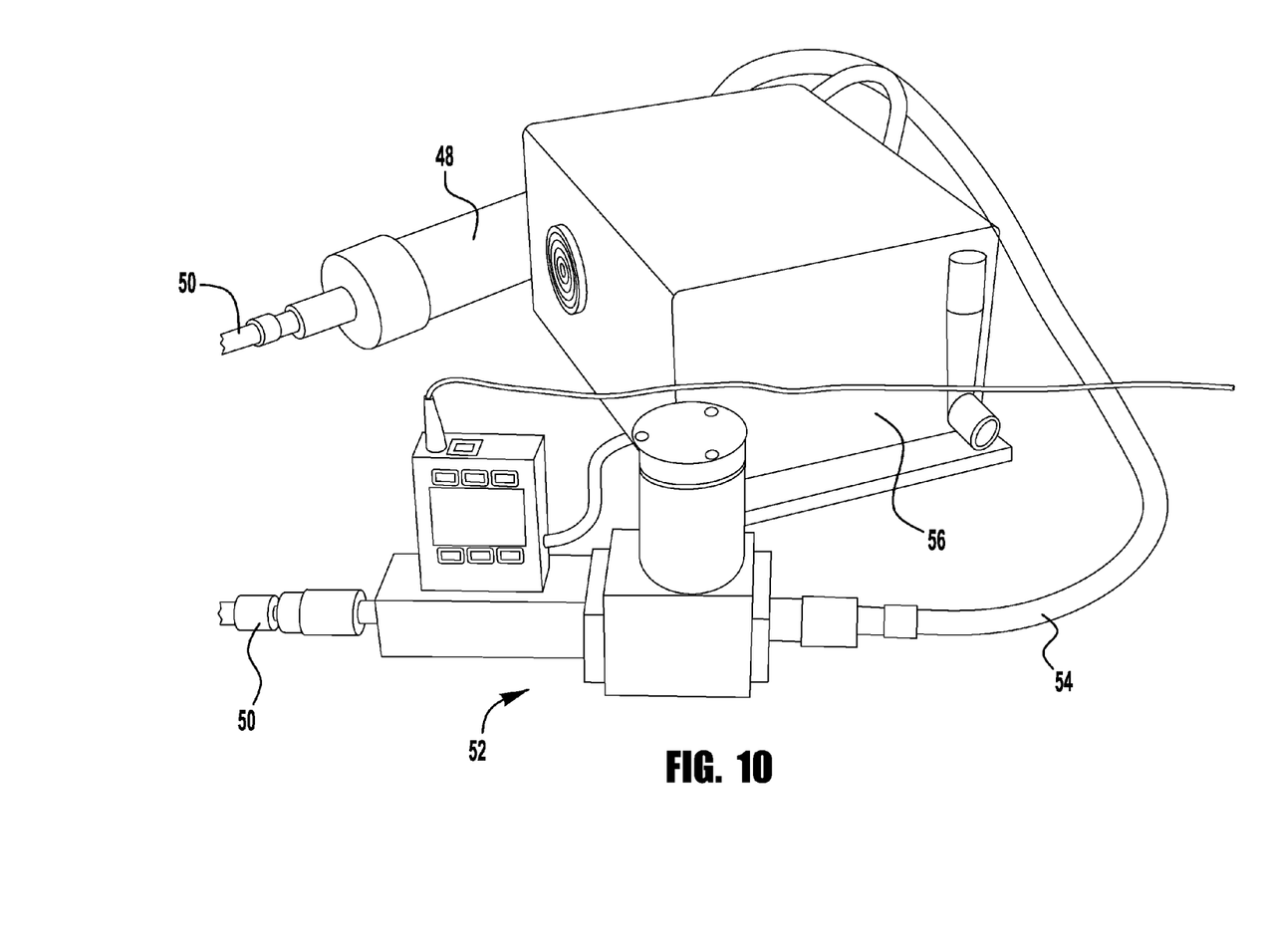
FIG. 10 is an illustration of a dual-range pump station, in accordance with the present invention.

The hot sample gas is withdrawn from measurement cell 94 through outlet port 122 into line 42 by a pump station 56, as shown in FIGS. 1 and 10. The line 42, as shown in FIG. 9, delivers the hot sample gas to a thermo-electric cooled exhaust gas conditioner 44.

Referring to FIG. 9, there is shown a thermo-electric cooled, exhaust gas conditioner 44 having an inlet 130 which receives the heated exhaust gas from line 42. The heated exhaust gas then flows through a line 132 connected to one end of a heat exchanger 134 and then into a line 136 which connects from the heat exchanger to an outlet 138. The heat exchanger 134 quickly cools off the heated exhaust gas received from the measurement cell 94. The exhaust gas conditioner 44 can be an open container 140 that contains water or some other cooling liquid. This fluid can be kept cool by a Peltier thermoelectric cooler 142 mounted outside of the container 140 with a thermal "finger" 144 which passes through the wall of the container to transfer heat from the cooling fluid to the Peltier thermoelectric cooler. The thermoelectric cooler 142 can be controlled by a temperature controller if necessary and can be helped by adding ice or fresh cool fluid to the cooling fluid within the container 140. The exhaust gas conditioner 44 can also be used without the thermoelectric cooler 142 if desired and appropriate. The heat exchanger 134 is oriented such that the flow of exhaust gas is not impeded by condensate.

The thermo-electric cooled, exhaust gas conditioner 44 has a gas-to-water heat exchanger 134 that is immersed in water or other cooling fluid that is kept cool by a Peltier thermoelectric cooler 142. The heat exchanger 134 can incorporate a drain valve (not shown) to occasionally purge the heat exchanger of condensate. However, it is noted that the drain valve is not needed for the operation of the preferred embodiment.

The exhaust gas conditioner 44 is preferably located close to the furnace exhaust through outlet port 122 so that the excess moisture in the sample gas condenses quickly thus minimizing any flow variations at the time when the mercury is being released from the sample. The exhaust gas conditioner 44 also cools the sample exhaust gases to a relatively consistent temperature that helps improve precision in flow and hence analyzer precision. Moisture in samples and especially aqueous standards for analysis can cause variations in flow and hence response as water expands and contracts as it changes state from water to steam and back again to water. The exhaust gas conditioner 44 minimizes the effect of this variation in flow.

As shown in FIGS. 1, 9 and 10, the flow of exhaust gas from the outlet port 138 of exhaust gas conditioner 44 flows through a line 46 into a filter 48 which contains soda lime, iodinated charcoal and or charcoal to scrub the exhaust gases of acid gases and mercury. The exhaust gas continues through line 50 into a mass flow controller 52 such as an Alicat Whisper series laminar flow element mass flow controller, that can precisely control the flow despite the system's inherent low differential pressure. The mass flow controller 52 has the ability to regulate flow by mass or volume.

The exhaust gas continues from the mass flow controller 52 and into a vacuum pump station 56 through a line 54. The pump station 56 induces the flow of gas through the furnace 100 and the measurement cell 94. The exhaust gas exits the pump within the pump station 56 though a muffler which suppresses the noise of the exhaust. The pump station 56 includes a high powered pump which can pump >20 liters/minute while the present embodiment may often only require a flow rate of a fraction of this amount. Therefore, the pump station 56 includes an air inlet (not shown) that can be controlled to allow more or less air into the pump to mix with the gases from line 54 to prevent the pump from "throttling" at such low flows.

The thermal desorption furnace 100, as shown in FIG. 6, has many features that make it unique and make the analysis of samples (especially sorbent traps for mercury) easier and with improved precision and accuracy.

Since the heating coils 104 and 106 are electrically insulated from the sample desorption tube 100, the sample desorption tube can be made of durable metal which should never break or leak like a sample tube of quartz or ceramic.

The inclusion of two heat zones 102a and 102b (compare 26 and 28 in FIG. 1), in furnace 100, as described above, helps with the analysis of high concentration samples.

The inclusion of an exhaust gas conditioner 44 for the sample gases exiting from the outlet 122 of the thermal analysis cell 94 quickly forces the condensation of water vapor in the sample effluent and allows more uniform control of the gas temperature going to the laminar flow element mass flow controller and vacuum pump to thereby provide more precise flow and hence better analytical results.

The thermoelectric cooler 142 can be controlled by a temperature controller if necessary and can be helped by adding ice or fresh cool fluid to the cooling fluid within the container 140. The exhaust gas conditioner 44 can also be used without the thermoelectric cooler 142 if desired and appropriate.

Operation

The furnace (100) is used when measuring the amount of mercury present in a sample placed into the sample boat (30), including higher level aqueous samples, complex samples such as oils, solid samples including sorbent traps used to measure the mercury content of emission sources, and gas streams introduced into the furnace directly.

For the analysis of higher-level aqueous samples, complex samples such as oils, and solid samples other than sorbent traps, the desired amount of sample is measured by mass or volume and placed directly into the sample boat or onto a bed of mercury-free charcoal that is first placed in the boat. The sample is then covered with a layer of sodium carbonate and placed in the furnace for analysis.

Figure 12:
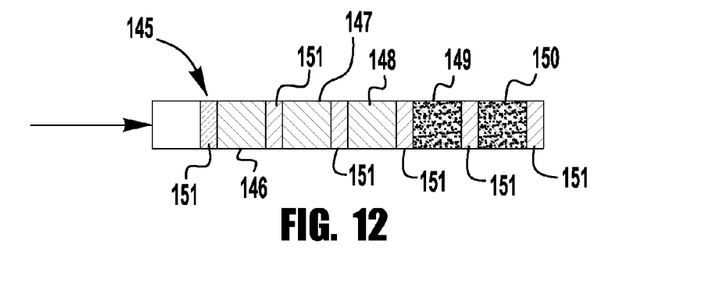
FIG. 12 is a side view of a speciation trap, in accordance with the present invention.

The furnace 100 is particularly useful when analyzing sorbent traps, such as a speciation trap 145. A sorbent trap such as the speciation trap 145 can be a glass tube with different sections of media separated by glass wool 151. For example, section 146 can be filled with an acid gas scrubber, sections 147 and 148 can be filled with potassium chloride and sections 149 and 150 can be filled with iodinated carbon. Each section 146, 147, 148, 149 and 150 can be enclosed on either side with glass wool 151. In operation, the contents of the trap are removed and each individual section along with the glass wool that precedes it is placed in a sample boat 30 and covered with sodium carbonate and analyzed. In the case of the potassium chloride sections, they are wrapped in aluminum foil along with the glass wool that precedes them before being placed in the sample boats 30 and then covered with sodium carbonate. This prevents the sodium carbonate and potassium chloride from mixing and allows the samples to be analyzed more quickly at higher temperatures. Transferring the contents of the sorbent traps to the sample boats can be tedious and the use of larger sample boats in this design makes this process easier.

Also, with the sample boats of previous designs, their small volume makes it difficult or impossible to wrap the potassium chloride sections in foil and still have room in the sample boats to cover them with sodium carbonate. Therefore, the potassium chloride sections cannot be analyzed at higher temperatures without the two compounds, i.e., the potassium chloride and the sodium carbonate, fusing together and also fusing to the sample boat requiring a difficult cleanup. Accordingly, with the sample boats of previous designs, it takes much longer to analyze the potassium chloride sections that have been covered with sodium carbonate at the required lower temperatures. Overall, speciation traps can be analyzed in as little as half the time using the analyzer system 10 of the preferred embodiment as compared to the systems requiring the use of small volume, sample boats of previous designs.

A sample boat 30 with the media from one section and covered with sodium carbonate is then inserted into the opening 102c of the sample desorption tube 102. A flow of about 0.5 L/min to about 20 L/min can be used in this design allowing a variability of sensitivity at a factor of >40.

Typical samples might be analyzed with both zones 102a and 102b heated by coils 104 and 106, respectively, for example at 680 degrees C. For the analysis of high-level samples, the sample boat 30 can be first placed in the first heated zone 102a heated by coil 104 that could be set at a low temperature, such as 480 degrees C. Once enough mercury has been released, as indicated on the computer 14 so that the analyst is confident that the detector 12 will not be over-saturated, the boat is moved further into the higher temperature heated zone 102b heated by coil 106, such as at 680 degrees C. In this way, these high-level samples can be analyzed in a fraction of the time as compared to previous designs that used a ramping feature on the furnace to lower and raise the furnace temperature.

Also, using the sample desorption tube 102 with two heated zones 102a and 102b heated by different heat coils 104 and 106 capable of two separate temperatures is advantageous when analyzing samples of various types, some requiring analysis at low temperatures and some requiring analysis at high temperatures because samples requiring analysis at lower temperatures can be analyzed solely in the first heated zone, such as at about 590 degrees C. While with other samples best analyzed at higher temperatures, they can be analyzed using the hotter second heated zone using the same calibration and without having to wait for a single heated zone to cool down and heat up. With these two zones set at constant temperatures throughout an analytical session, the analyzer system 10 is more precise than one that ramps the temperatures from cooler to hotter because such ramping affects the flow of the sample gases.

Since high-level samples can be analyzed at flow rates of 20 L/min or more, they can be done isothermally in minimal time, as little as 90 seconds, compared to using a low flow rate of approximately 4 L/min which requires having to ramp the furnace to slow the mercury elution which can take as long as 15-20 minutes per sample.

The external isolated heater coils 104 and 106 are virtually maintenance-free and don't become choked with debris as with the prior art internal "live" coils.

Having two independent heated zones 102a and 102b and duplicate heating coils, thermocouples, relays, and PID temperature controllers means that a failure of any component can be overcome in use by best configuring the remaining pieces to allow the instrument's continued use. This is a significant reliability advantage especially if the instrument is used in the field where repairs might be more difficult.

Figure 13:
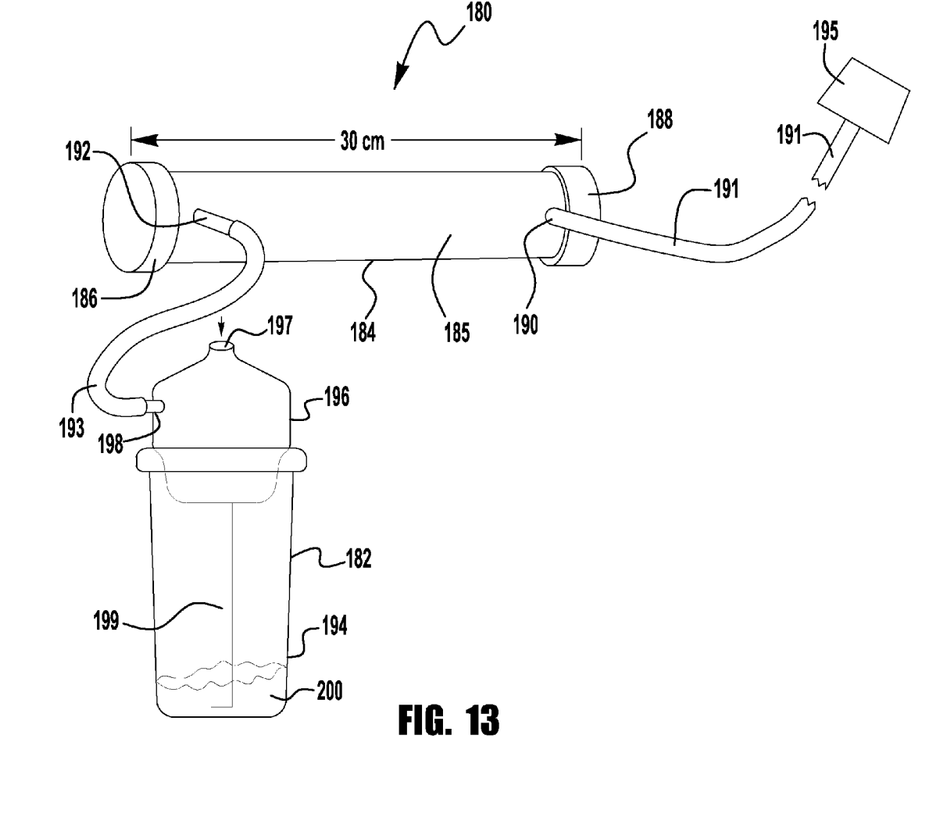
FIG. 13 is a schematic of an aqueous sample device, in accordance with the present invention.

Referring to FIG. 13, there is illustrated a schematic of an aqueous sample device 180 that uses a larger reaction vessel or impinger 182 to get better detection limits. The aqueous sample device 180, as shown in FIG. 13, consists of a measurement cell 184 which includes a tube 185 made of a material that resists the adsorption of mercury. The length of tube 185, when used with a suitably configured long optical bench, would be about 30 cm long. Alternatively, if the tube 185 is used with the standard optical bench shown, its length would be about 10 cm long. The tube 185 is sealed on both ends with lenses 186 and 188 made of quartz or another material transparent to the wavelengths of the beam(s) used, with an outlet 190 on one side that is connected through line 191 to a vacuum pumping system 195 (compare pump system 56 shown in FIG. 10) and an inlet 192 on the other side connected by a line 193 to an impinger 182 where aqueous samples are introduced and mixed with a stannous chloride solution by the turbulence of the incoming air. The impinger 182 includes a vessel 194 closed with a cap 196 having an air inlet 197 and an outlet 198. A tube 199 extends from the air inlet to the stannous chloride solution 200 disposed in the bottom of vessel 194.

An optical bench similar to optical bench 16 is mounted to a mercury vapor analyzer, such as described previously, in a path traveled by the analytical beams projected out of the vapor analyzer whereby the analytical beams traverse the measurement cell, interact with the sample effluent of the impinger directed into the cell from the outlet of the impinger and out of the cell through the outlet of the cell.

The aqueous sample device 180 is unique in that the measurement cell 184 is made to easily fit in either a larger configured optical bench or the standard optical bench, as shown in FIG. 2, which can also be used for the analysis of samples of other matrices. In either case, detection limits are much lower than achieved by using the standard cell, approximately 6 cm in length, because the measurement cell for this instrument uses the dual path optical bench instead of the single path optics used for the standard 6 cm cell.

For aqueous samples, a standard stannous chloride reduction system is used. The length of the larger configured optical bench is designed to be long enough to allow low concentration (<1 ng/L) water sample analysis in a robust measurement cell 180. For example, the analyzer 12 can be used for this analysis by using its internal multi-pass cell. But, whereas if liquid water is accidentally allowed to enter the cell, many thousands of dollars of damage can take place, and therefore, with the present invention, the measurement cell is designed so that it can simply be cleaned and dried.

The present invention can also be made to work in the detection of any metal that entirely converts to the gaseous phase and elemental form at the temperatures the oven is capable of generating. Whereas mercury is very unique because it is a liquid at ambient temperature, other metals such for example, selenium might also be measured in this way.

With respect to concentration limits of mercury analysis, the main advantage of the present attachment invention is the ease with which the limits can be reached. That is to say, detection limits are not much improved, but, in it's final form, the present invention will be able to quantify samples at a level of ½ to ¼ of any present commercial mercury analysis unit, which isn't a significant improvement given that quantification limits are already on the order of 100 or 200 picograms of mercury. However, one advantage of the present attachment is that the sample boats 30 can be much larger than those that are presently used, which perforce means that the detection limits in the terms of concentration will be lower with the present embodiment because more sample material can be placed in the boat. For example, the sample boat can have an elongated opening 30 as seen in FIGS. 8A and 8B of 13 mm by 80 mm and an internal diameter of 14 mm, and a length of between 19 cm and about 24 cm and a diameter of between 16 mm and about 20 mm. This compares to a typical sample boat of previous designs with openings of 5 mm by 76 mm and an internal diameter of 7 mm.

On the upper end of the detection scale, the preferred embodiment can quantify 100,000 ng (i.e., 100 ug). It could even be configured to handle larger samples and higher detection limits, were that deemed to be worthwhile. That is to say, while the current commercial units can analyze 100,000 ng, each analytical run takes on the order of 15 minutes. By contrast, the preferred embodiment is designed to do the same analysis in 3 to 4 minutes. In use, if 30 or more samples plus about 6 standards are to be analyzed, there is a huge efficiency improvement in analysis turn-around time.

Additionally, when analyzing speciation traps with trap sections made of potassium chloride (KCl), as shown in FIG. 12, these samples must be analyzed at lower temperatures (typically 590 degrees Celsius) in analyzers that are currently on the market so that the KCl doesn't fuse with the sodium carbonate that is put on all samples. By contrast, with the preferred embodiment, the boats are large enough that the KCl sections can be rolled in aluminum foil before placing them in the boats and then covered in sodium carbonate and analyzed at a higher temperature (680 degrees Celsius). With this arrangement, the KCl and Sodium carbonate never mix. Analysis of samples of this type can be done in half the time compared to prior art instruments because of this feature.

The thermal method of mercury analysis is enormously better than other techniques especially when combined with an atomic absorption spectrometer employing Zeeman correction. Samples can be analyzed in seconds or minutes with no or little sample preparation. Large manufacturers of analytical equipment, such as Teledyne Lehman of Hudson, N.H., have tried to enter this market but failed. Lumex and Ohio Lumex pretty much monopolize the present market, and lots of mercury work is being done around the world. The preferred embodiment is much more efficient in terms of time saved and ease of maintenance; it can analyze samples in a fraction of the time with less work, and is more precise as well.

Typical analyzers for this type of analysis have very small sample boats that limit sample volume and make it time consuming and difficult to place the sample in the boat. For the analyzer system 10, since the sample desorption tube 102 is so large, at least 1.5 inches in diameter, is made of metal, and incorporates heater coils that are electrically insulated and wound about the outside of the sample desorption tube, the sample boats can be made of stainless steel or other durable metal and can be large enough that sample preparations take less than half the time or better.

Flow through the analyzer dictates response and during the course of analysis it is important that the flow is consistent. Also, the ability to analyze at low flows (<1.0 L/min) helps with low-level analysis and the ability to analyze at high flows (>4 L/min, up to 20 L/min or more) makes the analysis of high-level samples more efficient. The analyzer system 10 uses a unique combination of a laminar flow element-mass flow controller 52 and a specially designed pump station 56 to allow precise instrument flow at all flow rates. Also incorporated in the flow path is a muffler to quiet the pump exhaust and a filter to scrub the instrument's exhaust of mercury and acid gases.

Flow is initially induced through the system 10 by the use of a Rolling Diaphragm vacuum pump (not shown) disposed within the pump station 56. The Rolling Diaphragm vacuum pump is fitted with a dual ball bearing motor shaft to add reliability and long life. The exhaust from the vacuum pump is directed into an "L"-shaped muffler (not shown) to dampen the pump's noise. The vacuum pump is also mounted to the pump box in an isolated fashion and surrounded by sound insulating materials and suitably positioned sound baffles to limit noise. A fan in the pump box keeps the vacuum pump cool and helps direct exhaust out of the enclosure.

The vacuum pump's inlet is connected to a fitting splitting the inlet flow between two paths; one is to a valve and meter open to atmosphere that can be adjusted from a flow of zero to maximum flow. The other is connected to the laminar flow element mass flow controller 52, which can precisely control the flow according to mass or volume as chosen on its keypad. In use, a suitable instrument flow is selected on the control pad of the laminar flow element mass flow controller 52 and if this rate is small compared to the maximum flow of the pump (for example, less than 10 L/min), the valve on the other meter is open to allow the vacuum pump to pull air through this path as well to avoid having the pump "throttled" by operating at too low a flow rate. The laminar flow element mass flow controller can regulate the flow through the instrument from <1.0 L/min to over 20 L/min. The other valve is adjusted to prevent the pump "throttling" but to be restrictive enough so that the laminar flow element mass flow controller 52 can achieve its desired setting.

The inlet of the laminar flow element mass flow controller 52 is connected to a filter element 48 that contains iodinated charcoal and, or charcoal to scrub the instrument's exhaust of mercury and other effluents and soda lime to assure that no acid gases reach the laminar flow element mass flow controller 52 or pump.

This instrument can also be used for discrete or continuous measurement of mercury (or other suitable analytes) in gas streams such as emission sources by directing either a diluted or undiluted flow of the gas stream in question into the sample desorption tube making sure that the volume of gas introduced is less than the volume of gas exiting the furnace to assure none of the sample is lost by exiting the entrance.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

The invention claimed is:

1. An analyzer system for measuring mercury, comprising:
   a mercury vapor analyzer for generating and detecting analytical beams;
   a furnace mounted to a measurement cell;
   a sample boat to contain a samples adapted to be disposed within the furnace to release a sample effluent gas from the samples into the measurement cell;
   an optical bench mounted to the mercury vapor analyzer into which the measurement cell can be positioned so that the analytical beams can traverse the measurement cell, interact with the sample effluent gas and return to the vapor analyzer where the amount of mercury in the sample effluent gas can be determined;
an exhaust gas conditioner that includes a heat exchanger which receives and cools the heated exhaust gas from the measurement cell so as to condense any excess moisture carried in the sample gas, and a thermoelectric cooler to cool fluid within the exhaust gas conditioner; and
a pump station to draw the sample effluent gas from the measurement cell.

2. The analyzer system of claim 1 wherein the optical bench includes:
a hollow tube mounted at a first end of the optical bench through which the analytical beams projected out of the vapor analyzer are directed through the measurement cell being positioned in said optical bench mounted to the mercury vapor analyzer;
a prism mounted at a second end of the optical bench for returning the analytical beams that traversed the measurement cell to the analyzer;
and wherein the optical bench is adapted for use with a thermal sampling device.

3. The analyzer system of claim 2 further including a lens to direct the analytical beams returning from the prism through the hollow tube to an optical detector in the analyzer.

4. An analyzer system for measuring mercury, comprising:
a mercury vapor analyzer for generating and detecting analytical beams;
a furnace mounted to a measurement cell;
a sample boat to contain a sample adapted to be disposed within the furnace to release a sample effluent gas from the sample into the measurement cell;
an optical bench mounted to the mercury vapor analyzer into which the measurement cell can be positioned so that the analytical beams can traverse the measurement cell, interact with the sample effluent gas and return to the vapor analyzer where the amount of mercury in the sample effluent gas can be determined;
an elongated sample desorption tube connected to the measurement cell, the sample desorption tube having an opening to receive the sample boat,
the sample desorption tube being large enough that a high flow rate between about 4 L/minute and 40 L/minute does not sweep the sample out of the sample boat disposed within the sample desorption tube; and
a pump station to draw the sample effluent gas from the measurement cell.

5. The analyzer system of claim 4 further including a flow modifier in the tubular fitting to induce turbulent flow in the heated sample effluent gas passing from the sample desorption tube to the measurement cell.

6. The analyzer system of claim 4 wherein:
a first bendable resistance-heating coil is wrapped around the outside of a first section of the sample desorption tube; and
a second bendable resistance-heating coil is wrapped around the outside of a second section of the sample desorption tube.

7. The analyzer system of claim 6 wherein the first and second resistance-heating coils are connected to a furnace controller for controlling the temperature in each of the first and second sections.

8. The analyzer system of claim 1 wherein:
the sample boat (30) is a tube (29) closed at either end and having an elongated opening therebetween forming an open slot between the closed ends of the tube to receive the sample to be analyzed.

9. The analyzer system of claim 7 wherein the measurement cell is sealed on both ends by gaskets and windows transparent to the wavelengths used held in place with screw caps.

10. The analyzer system of claim 1 wherein the exhaust gas conditioner includes: a heat exchanger which receives and cools the heated exhaust gas from the measurement cell so as to condense any excess moisture carried in the sample gas; and a thermoelectric cooler to cool fluid within the exhaust gas conditioner.

11. The analyzer system of claim 10 further including a filter to receive the cooled sample gases from the exhaust gas conditioner and to scrub the sample gases of acid gases and mercury.

12. The analyzer system of claim 11 further including a laminar flow element mass flow controller that receives the cooled sample gases from the filter and regulates the flow of gas through the analyzer system despite the low differential pressure between an inlet and outlet of the mass flow controller.

13. The analyzer system of claim 1 wherein:
the pump station induces the flow of sample gas through the furnace and the measurement cell;
the pump station is plumbed in such a way that it can operate at high and low flow rates (<1.0 L/min to >20 L/min).

14. A method for measuring mercury vapor, comprising:
generating analytical beams with a mercury vapor analyzer;
releasing heated sample effluent gas from a sample heated in a sample boat disposed within a furnace into the measurement cell;
projecting the analytical beams from the vapor analyzer through the measurement cell to interact with the heated sample effluent gas and returning the analytical beams back to the vapor analyzer where the amount of mercury in the heated sample effluent gas can be determined;
drawing the heated sample effluent gas from the measurement cell;
cooling the sample gas drawn from the measurement cell so as to condense any excess moisture carried in the sample gas; and
cooling the sample gas drawn from the measurement cell to near ambient for improved regulation of the gas drawn from the measurement cell.

15. A method for measuring mercury vapor, comprising:
generating analytical beams with a mercury vapor analyzer;
releasing heated sample effluent gas from a sample heated in a sample boat disposed within a furnace into the measurement cell;
projecting the analytical beams from the vapor analyzer through the measurement cell to interact with the heated sample effluent gas and returning the analytical beams back to the vapor analyzer where the amount of mercury in the heated sample effluent gas can be determined; and
drawing the heated sample effluent gas from the measurement cell;
heating the sample boat within a furnace having a first heating section and a second heating section; and separately controlling the temperature in each of the first and second heating sections.

16. A method for measuring mercury vapor, comprising:
generating analytical beams with a mercury vapor analyzer;
releasing heated sample effluent gas from a sample heated in a sample boat disposed within a furnace into the measurement cell;
projecting the analytical beams from the vapor analyzer through the measurement cell to interact with the heated sample effluent gas and returning the analytical beams back to the vapor analyzer where the amount of mercury in the heated sample effluent gas can be determined; and
drawing the heated sample effluent gas from the measurement cell;
wrapping potassium chloride sections of a speciation trap in a foil;
placing the foil wrapping the potassium chloride sections in a boat; and
covering with sodium carbonate.

17. The method of claim 16 further including regulating the flow of gas through the analyzer system with a laminar flow element mass flow controller despite a low differential pressure between an inlet and outlet of a mass flow controller.

18. The analyzer system of claim 1 wherein the sample boat is constructed of stainless steel.

19. The analyzer system of claim 18 wherein the sample boat has a length of between 19 cm and about 24 cm and a diameter of between 16 mm and about 20 mm.

20. The analyzer system of claim 13 wherein the pump is a rolling diaphragm pump with a dual ball bearing motor shaft.

21. The analyzer system of claim 1 further comprising an elongated sample desorption tube connected at one end to the measurement cell, and having an opening at an opposite end to receive the sample boat.

22. The analyzer system of claim 21 further comprising a first bendable resistance-heating coil wrapped around the outside of a first section of the sample desorption tube, and a second bendable resistance-heating coil is wrapped around the outside of a second section of the sample desorption tube.

* * * * *